US010376330B2

(12) United States Patent
Guo et al.

(10) Patent No.: US 10,376,330 B2
(45) Date of Patent: Aug. 13, 2019

(54) MOLDED CONTAINER FOR TISSUE SCAFFOLDS

(71) Applicants: NATIONAL CHENG KUNG UNIVERSITY, Tainan (TW); NATIONAL CHENG KUNG UNIVERSITY HOSPITAL, Tainan (TW)

(72) Inventors: How-Ran Guo, Hsinchu (TW); Chao-Lin Chen, Taichung (TW); Jin-Jia Hu, Hsinchu (TW)

(73) Assignees: National Cheng Kung University, Tainan (TW); National Cheng Kung University Hospital, Tainan (TW)

( * ) Notice: Subject to any disclaimer, the term of this patent is extended or adjusted under 35 U.S.C. 154(b) by 308 days.

(21) Appl. No.: 15/479,460

(22) Filed: Apr. 5, 2017

(65) Prior Publication Data
US 2018/0055594 A1 Mar. 1, 2018

(30) Foreign Application Priority Data
Aug. 23, 2016 (TW) .............................. 105126957 A

(51) Int. Cl.
*A61B 50/30* (2016.01)
*B65D 30/08* (2006.01)
(Continued)

(52) U.S. Cl.
CPC .............. *A61B 50/30* (2016.02); *A61B 50/31* (2016.02); *B65D 31/02* (2013.01); *B65D 33/04* (2013.01);
(Continued)

(58) Field of Classification Search
CPC ................................. B65D 33/04; B65D 33/14
(Continued)

(56) References Cited

U.S. PATENT DOCUMENTS 4,810,376 A * 3/1989 Magasi ............... A61M 1/3643
210/136
4,872,553 A * 10/1989 Suzuki ................. A61J 1/1462
206/524.4
(Continued)

FOREIGN PATENT DOCUMENTS

CN 103357069 A 10/2013
CN 104842560 A 8/2015
TW I432230 B 4/2014

*Primary Examiner* — J. Gregory Pickett
*Assistant Examiner* — Tia Cox
(74) *Attorney, Agent, or Firm* — Rosenberg, Klein & Lee

(57) ABSTRACT

A molded container for a tissue scaffold is provided. The molded container comprises a bag made from a soft material, a shape memory frame, and an inner support tube. A sealing part is disposed on the opening of the bag, and an operation window is disposed on the lower part of the bag. The sealing part is closed when no external force is applied. The shape memory frame is embedded in the bag. At least two adjustable hooks are disposed on the ends of the shape memory frame. The inner support tube is disposed on the inner bottom of the bag and selectively penetrates a molded accommodation volume for forming a tissue scaffold. The length of the inner support tube is more than the length of the molded accommodation volume. Therefore, the molded container for a tissue scaffold has features of portability, adjustability, sterility, convenience, and stability.

9 Claims, 5 Drawing Sheets

(51) Int. Cl.
*B65D 33/04* (2006.01)
*B65D 33/14* (2006.01)
*A61B 50/31* (2016.01)
*A61B 17/00* (2006.01)

(52) U.S. Cl.
CPC .... *B65D 33/14* (2013.01); *A61B 2017/00867* (2013.01); *A61B 2050/3012* (2016.02); *A61F 2240/00* (2013.01)

(58) Field of Classification Search
USPC ......................................................... 206/438
See application file for complete search history.

(56) References Cited

U.S. PATENT DOCUMENTS

| | | | | |
|---|---|---|---|---|
| 4,976,707 A * | 12/1990 | Bodicky | ............ | A61M 5/1483 604/319 |
| 5,263,929 A * | 11/1993 | Falcone | ............ | A61M 5/445 126/263.07 |
| 5,306,269 A * | 4/1994 | Lewis | ............ | A61M 1/0209 604/403 |
| 5,843,049 A * | 12/1998 | Heilmann | ............ | A61J 1/10 604/275 |
| 5,896,989 A * | 4/1999 | Ropiak | ............ | A61J 1/10 206/438 |
| 6,364,864 B1 * | 4/2002 | Mohiuddin | ............ | A61J 1/10 206/219 |
| 6,575,954 B1 * | 6/2003 | Ravizza | ............ | A61M 5/14 206/216 |
| 8,684,991 B2 * | 4/2014 | Wyss | ............ | A61M 5/148 604/410 |
| 2009/0209031 A1 * | 8/2009 | Stopek | ............ | A61B 17/06114 435/307.1 |
| 2013/0281964 A1 * | 10/2013 | Kugelmann | ............ | A61J 1/10 604/410 |
| 2014/0213765 A1 | 7/2014 | Lee | | |
| 2016/0051444 A1 * | 2/2016 | Muth | ............ | B31B 50/84 604/408 |

* cited by examiner

MOLDED CONTAINER FOR TISSUE SCAFFOLDS

BACKGROUND

Field of Invention

The disclosure relates to a molded container for a tissue scaffold. More particularly, the disclosure relates to a bag-shaped container having a special structure. This bag-shaped container is suitable to be used to mold various tissue scaffold. The bag-shaped container comprises at least one operation window, a shape memory frame, and an inner support tube. Therefore, the production of tissue scaffolds may have features of adjustability, portability, sterility, convenience, and stability.

Description of Related Art

In recent years, medicine is progressing. Many incurable diseases may be cured in nowadays. Although the pain caused by suffering disease is substantially decreased, many diseases still need doctors suture or repair damage tissues to perform a treatment. Some diseases even need living organ transplantation to achieve the purpose of repairing the patient's tissue. However, this approach usually has many limitations and inconvenience.

For solving this problem, "tissue engineering" or "regenerative medicine" is proposed. Tissues and organs might be initiatively regenerated, not only passively wait for human body donation. Tissue engineering has been developed for almost 30 years and progresses very rapidly. At present, similar tissues of bone, skin, cornea and others can be fabricated using tissue engineering.

Within the tissue engineering, a tissue scaffold has to be used to provide an environment for cell growth and tissue differentiation. The tissue scaffold is provided for the cell migration and cell growth therein. The tissue scaffold may contain cells, growth factors, extracellular matrix, drugs or chemicals, and cell growth, tissue differentiation and remodeling can thus be performed in vitro or in vivo to produce tissues that are useful in experimental uses or further in implantation applications. For example, patent TW 1432230 (B) discloses a tissue scaffold prepared from an acellular tissue matrix and sodium acetate. The acellular tissue matrix includes collagen, elastin, and vascular channels. The tissue scaffold may be used as a part of a wound treatment device that provides reduced pressure therapy. Patent US 20140213765 A1 discloses a tissue scaffold made of albumin having continuous solid networks and voids, so that the tissue scaffold can support cell attachment, growth, and differentiation, and directing new tissue formation.

However, nowadays in the use of tissue scaffold, it still has many inconveniences resulted from environmental limitations. Moreover, containers for tissue scaffolds are all large equipment, and thus there is a considerable inconvenience in the application and carrying.

SUMMARY

In view of the drawbacks above, the inventors develop this invention by the many-year manufacturing and design experience and knowledge in the related fields and ingenuity.

A molded container for a tissue scaffold is provided. The molded container has a bag having at least one operation window, a shape memory frame embedded in the bag, and an inner support tube disposed in the inner bottom of the bag. The inner support tube selectively penetrates the molded container having a molded accommodation volume for forming a tissue scaffold. The molded container has features of portability, adjustability, sterility, convenience, and stability.

In order to reach the purposes above, a molded container for a tissue scaffold is provided. The molded container comprises a bag made from a soft material, a shape memory frame, and an inner support tube. A sealing part is disposed on the opening of the bag, and an operation window is disposed below the sealing part. The sealing part is closed when no external force is applied. A cover disposed on the operation window can be peeled off or opened when using. The shape memory frame is embedded in the bag. At least two adjustable hooks are disposed on the ends of the shape memory frame and protruded out of the bag. The inner support tube is disposed on the inner bottom of the bag and selectively penetrates a molded accommodation volume for forming a tissue scaffold. The length of the inner support tube is more than the length of the molded accommodation volume.

In one embodiment of this invention, the front and rear surfaces each has at least one magnetic element disposed below the operation window correspondingly. The magnetic elements may close or open the operation window thereabove by magnetic attraction or repellence forces or assist the molding of the tissue scaffold. In addition, the magnetic elements can be disposed on the periphery of the molded accommodation volume of the molded container for assisting the tissue scaffold by the attraction and repellence of these magnetic elements, with the selectively addition of an external magnetic field or with a magnetic material within the tissue scaffold, such as microspheres.

In one embodiment of this invention, the inner support tube may be made from a soft or a hard material. The inner support tube may be a U-shaped inner support tube or a single-segment inner support tube.

In one embodiment of this invention, when the inner support tube is a U-shaped inner support tube, two top sides of the bag respectively have a flexible clamp for fixing the two ends of the U-shaped inner support tube. Two external sides of the bag respectively have a ruler for measuring a relative extending length of the two ends of the U-shaped inner support tube.

In one embodiment of this invention, when the inner support tube is a single-unbent-segment inner support tube, two bottom sides of the bag respectively have a fixing fixture for fixing the two ends of the single-unbent-segment inner support tube.

In one embodiment of this invention, the adjustable hooks have threaded structures for adjusting the bottom level of the shape memory frame.

In one embodiment of this invention, the molded accommodation volume is a cylindrical accommodation volume or other 3D steric structures.

In one embodiment of this invention, the bag has a liquid level indication line.

In one embodiment of this invention, the shape memory frame may be a metal frame comprising a shape memory metal material to maintain a fixed shape of the frame.

In one embodiment of this invention, the molded container is a sterile kit.

In one embodiment of this invention, a turning of the inner support tube has a fixed-point indication mark.

Therefore, this molded container can adjust the positions of the devices without directly contacting the devices in the bag to prevent foreign matter from coming inside to form a sterile environment. Hence, the cells inside will not be affected when the cells are cultured. Moreover, the clamps, the inner support tube, and the shape memory frame can be used to maintain the shape. Therefore, the bag will not collapse during the adjustment or use.

DETAILED DESCRIPTION

To more completely and clearly illustrate the technical means and effects of this invention, the detailed descriptions are set forth below. Please refer to the disclosed figures and the reference numbers.

Figure 1:
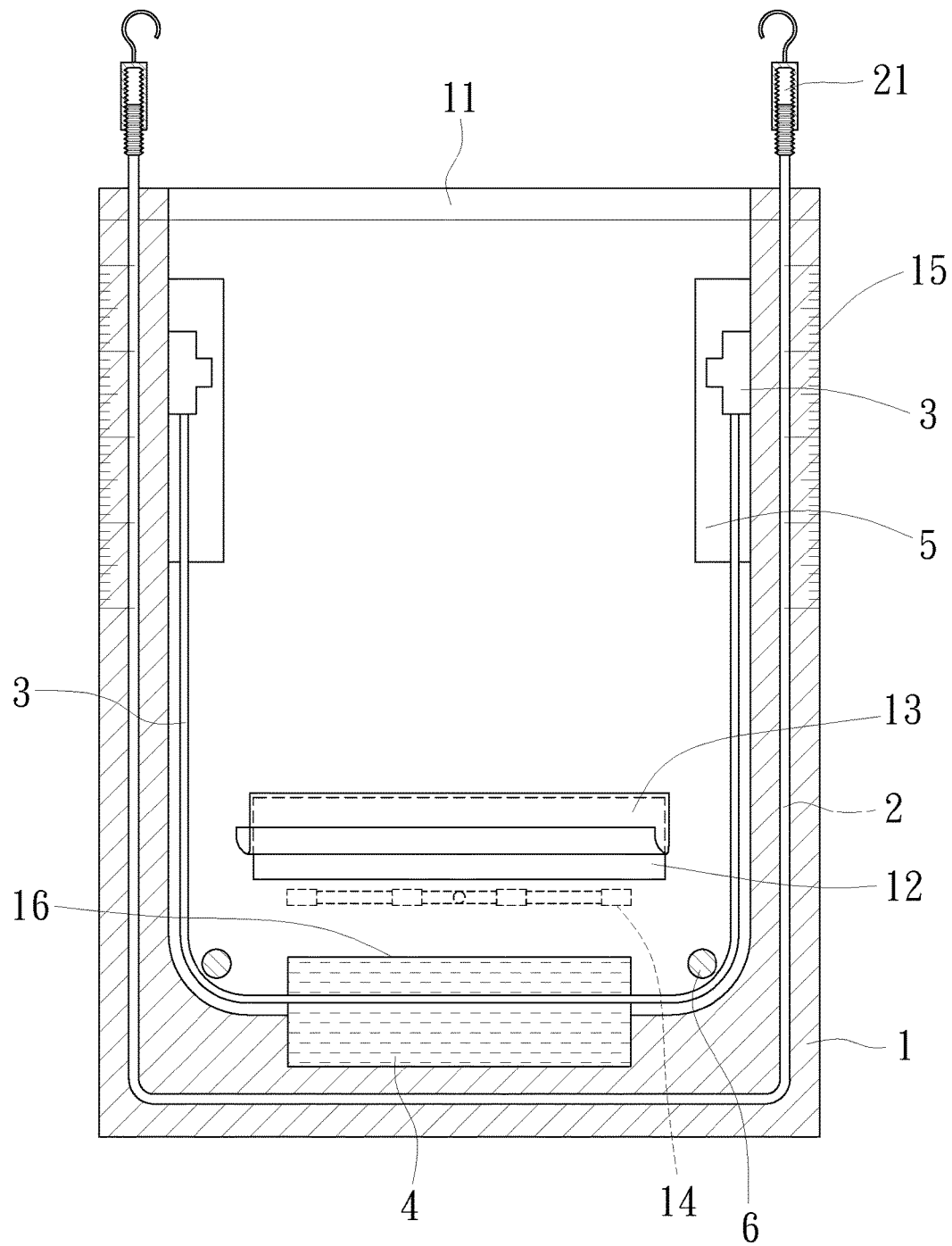
FIG. 1 is a cross-sectional diagram of a first embodiment of this invention.

First, please refer to FIG. 1, which is a cross-sectional diagram of a molded container for a tissue scaffold according to a first embodiment of this invention. The molded container comprises a bag 1 made from a soft material, a shape memory frame 2, and an inner support tube 3.

A sealing part 11 is disposed on the opening of the bag 1, and an operation window 12 is disposed below the sealing part 11. At least a magnetic element 14 is disposed on each of the front and rear surfaces of the bag 1 and below the operation window 12. The sealing part 11 is closed when no external forces are applied thereon. A cover 13 is disposed on the operation window 12, and the cover 13 can be peeled off or opened when the operation window 12 is used. A liquid level indicating line 16 is disposed on the external side of the bag 1.

The shape memory frame 2 is embedded in the periphery of the bag 1. The frame 2 is a metal frame made by a memory metal to maintain the shape of the frame 2. At least two adjustable hooks 21 are disposed on two top sides of the frame 2 and protruded out of the bag 1. The adjustable hooks 21 each has a threaded structure to adjust the bottom level of the shape memory frame 2.

The inner support tube 3 is disposed on the inner bottom of the bag 1 and penetrated into a molded accommodation volume 4 for forming a tissue scaffold. The molded storage volume 4 is a cylindrical accommodation volume or other 3D steric structures, and the length of the inner support tube 3 is longer than the length of the molded accommodation volume 4. The inner support tube 3 may be made from a soft or a hard material, for example.

The inner support tube 3 may be a U-shaped inner support tube. Two elastic clamps 5 are disposed on two top inner sides of the bag 1 for fixing the two terminals of the inner support tube 3. Two rulers 15 are disposed on two sides of the bag 1 to measure the relative extending length of the two terminals of the inner support tube 3. Fixed-point indication marks (not shown in FIG. 1) is disposed on the turnings of the inner support tube 3 for placing fixing fixtures 6. When the inner support tube 3 is placed, the inner support tube 3 and the fixing fixtures 6 can provide or decrease additional tension of the inner support tube 3 in the molded accommodation volume 4, and the shape of the inner support tube 3 can thus be maintained in the molded accommodation volume 4.

The front and rear surfaces of the bag 1 below the horizontal segment of the inner support tube 3 are laminated and sealed to support the inner support tube 3 thereon. This design can avoid the material of the tissue scaffold from overflowing out of the molded accommodation volume 4 to the space in the lower part of the bag 1.

Furthermore, the embodiments below can further prove the practice scope of this invention, but it is not intended to limit the scope thereto.

As shown in FIG. 1, the adjustable hooks 21 may be used to hang the bag 1 while using, and the threaded structures of the adjustable hooks 21 may be rotated to adjust the horizontal level of the shape memory frame 2.

When the inner support tube 3 is a U-shaped inner support tube, the inner support tube 3 may be placed on the bottom of the bag 1, and the two terminals of the inner support tube 3 may be fixed by the elastic clamps 5. If the inner support tube 3 is dropped, the external fixing fixtures 6 may be used to pull the inner support tube 3 outward. On the contrary, if the inner support tube 3 is too tight, the external fixing fixtures 6 may be used to push the inner support tube 3 inward. Therefore, the position of the inner support tube 3 can be fine-tuned to avoid the inner support tube 3 from being directly touched, and the infection opportunity can be decreased.

Figure 2:
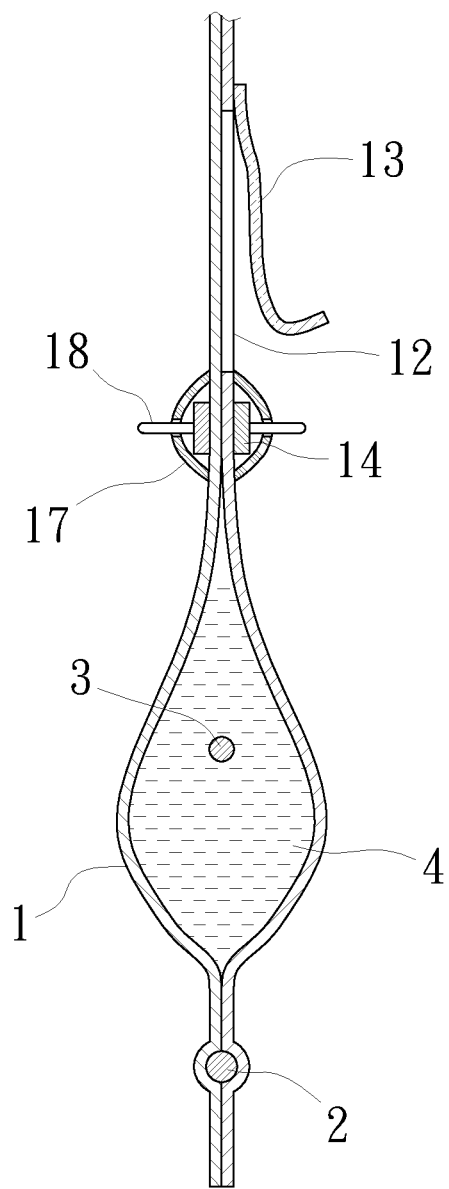
FIG. 2 is a local cross-sectional diagram of the first embodiment of this invention.

After the inner support tube 3 is fixed, the inner support tube 3 may selectively penetrate the molded accommodation volume 4 for forming a tissue scaffold, as shown in FIG. 2. The molded accommodation volume 4 is a cylindrical accommodation volume or other 3D steric structures. Other parts of the bag 1 are designed to be laminated and sealed. In operation, the needed material may be added through the operation window 12 to form the predetermined tissue scaffold. The magnetic elements 14 below the operation window 12 can quickly close the space above the molded accommodation volume 4 after the addition of the tissue material, so that they can start to react in pre-designed shape. After completing the reaction, the cover 13 may be torn apart along the dashed line to obtain the tissue scaffold and the inner support tube 3. Then, a subsequent experiment or application may be proceeded.

Please refer to FIG. 2. The magnetic elements 14 and fixing rods 17 thereof use a second layer of material to coat the bag 1. The magnetic elements 14 on the fixing side are disposed on the side opposite to the operation window 12, and the magnetic elements 14 on the moving side are disposed on the same side with the operation window 12. The magnetic elements 14 on the moving side can be slid to the left and right.

Figure 3:
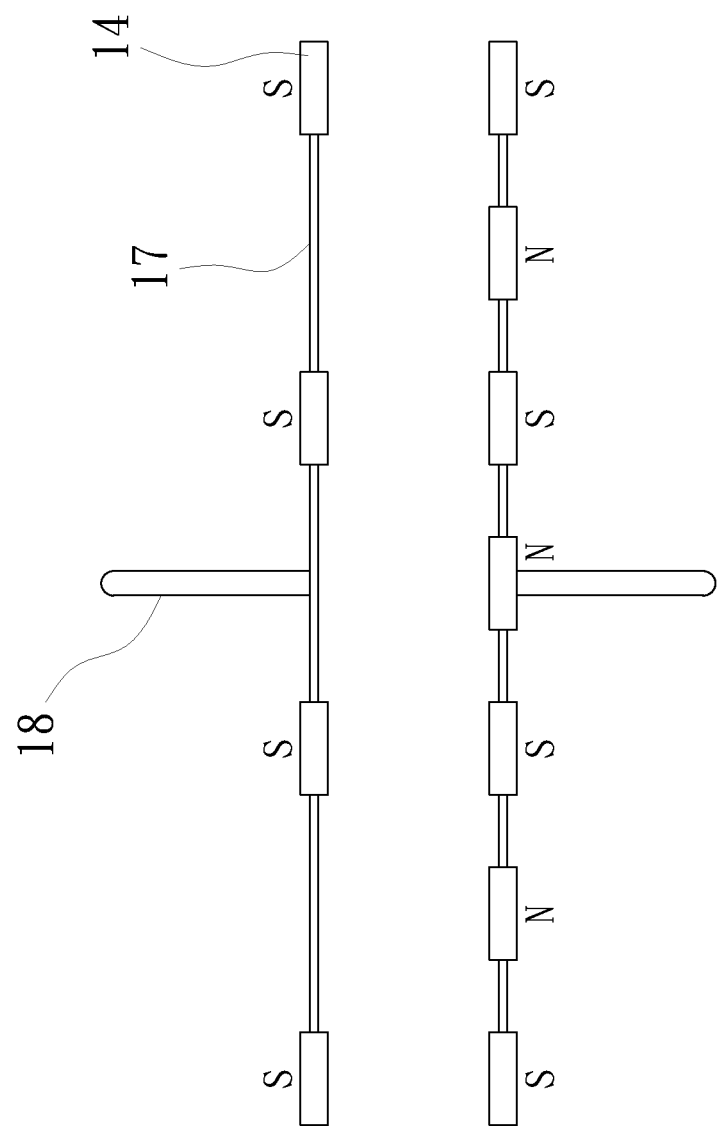
FIG. 3 is a partial diagram of the first embodiment of this invention.

As shown in FIG. 3, which is a diagram of the magnetic elements 14. The N and S pole sides of the magnetic elements 14 are alternatively arranged on the moving side, and the series of magnetic elements 14 are arranged on the fixing side. The magnetic elements 14 are all disposed on the fixing rods 17, and operation rods 18 are respectively disposed on the fixing rods 17. The magnetic elements 14 on the moving side are moved to the right or to the left to attract or repel the magnetic elements 14 on the fixing side by controlling the operation rods 18. Then, the anterior and posterior wall of the molded container around the magnetic elements 14 below the operation window 12 (not shown in FIG. 3) may be constantly spaced or approximated.

Figure 4:
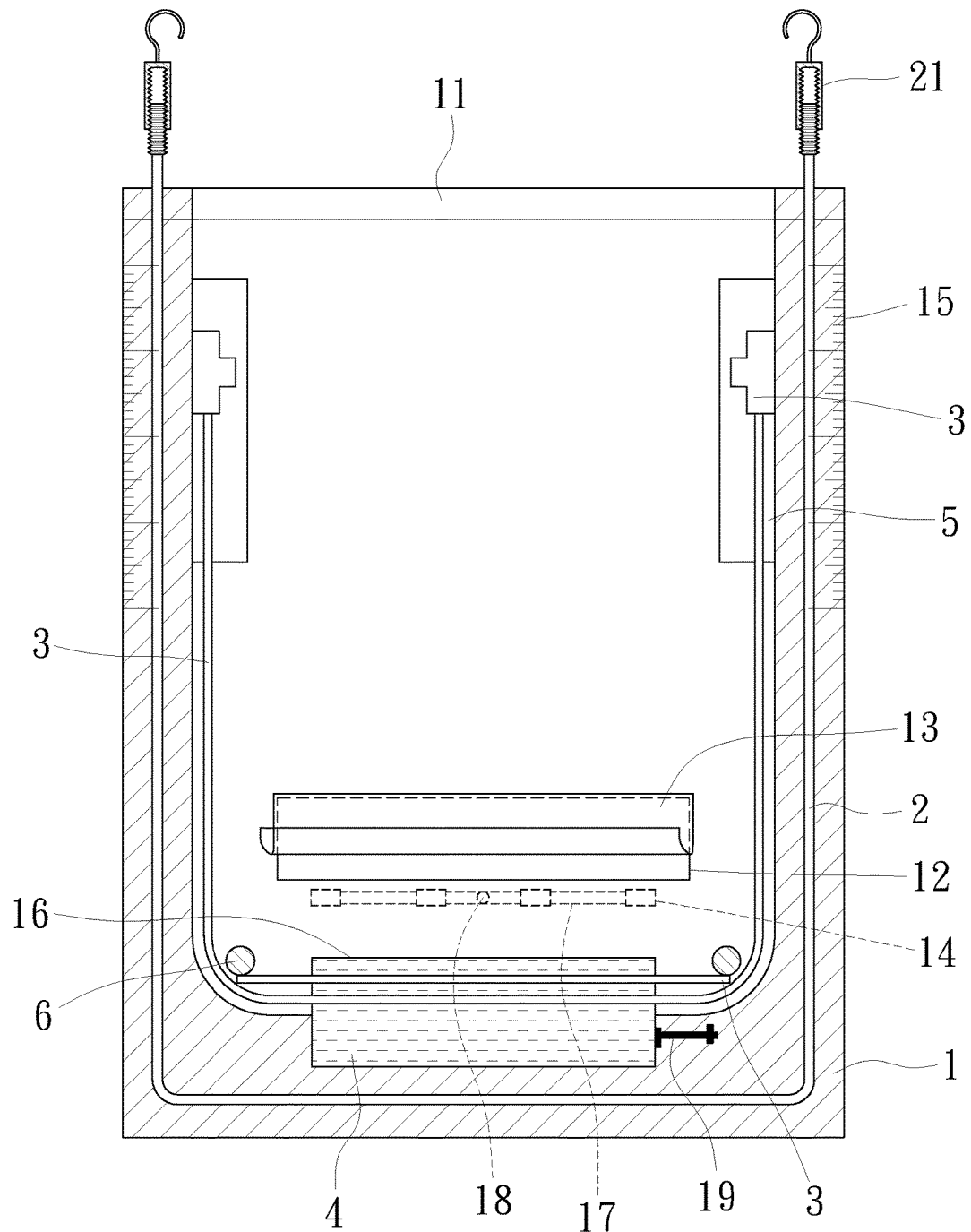
FIG. 4 is a cross-sectional diagram of a second embodiment of this invention.

Please refer to FIG. 4, which is a cross-sectional diagram of a molded container for a tissue scaffold according to a second embodiment of this invention. The molded container comprises a bag 1 made from a soft material, a shape memory frame 2, and an inner support tube 3.

A sealing part 11 is disposed on the opening of the bag 1, and an operation window 12 is disposed below the sealing part 11. At least a magnetic element 14 is disposed on each of the front and rear surfaces of the bag 1 and below the operation window 12. The sealing part 11 is closed when no external forces are applied thereon. A cover 13 is disposed on the operation window 12, and the cover 13 can be peeled off or opened when the operation window 12 is used. A liquid level indicating line 16 is disposed on the external side of the bag 1.

The shape memory frame 2 is embedded in the periphery of the bag 1. The frame 2 is a metal frame made by a memory metal to maintain the shape of the frame 2. At least two adjustable hooks 21 are disposed on two top sides of the frame 2 and protruded out of the bag 1. The adjustable hooks 21 each has a threaded structure to adjust the bottom level of the shape memory frame 2.

The inner support tube 3 is disposed on the inner bottom of the bag 1 and inserted into a molded accommodation volume 4 for forming a tissue scaffold. The molded storage area is a cylindrical accommodation volume or other 3D steric structures, and the length of the inner support tube 3 is longer than the length of the molded accommodation volume 4. The inner support tube 3 may be made from a soft or a hard material, for example.

The inner support tube 3 may be a U-shaped inner support tube. The two sides of the inner support tube 3 are turned from vertical to horizontal and further extending to a certain length to be inserted into the molded accommodation volume 4. Furthermore, a horizontal support segment 19 may be disposed in the bag 1. The horizontal support segment 19 in the bag 1 may be provided to dispose a single-unbent-segment inner support tube. Two fixing fixtures 6 are disposed on two bottom sides of the bag 1 for fixing the two ends of the single-unbent-segment inner support tube. Therefore, a user may use the single-unbent-segment inner support tube for forming a tissue scaffold. The inner support tube 3 in the molded accommodation volume 4 may have an irregular shape, such as cylindrical and triangular three-dimensional modeling, etc. The molded accommodation volume 4 may also have an irregular steric structure to fit the shape of the inner support tube 3.

Two elastic clamps 5 are disposed on two top inner sides of the bag 1 for fixing the two terminals of the inner support tube 3. Two rulers 15 are disposed on two sides of the bag 1 to measure the relative extending length of the two terminals of the inner support tube 3. Fixed-point indication marks (not shown in FIG. 4) are disposed on the turnings of the inner support tube 3 for placing the fixing fixtures 6. When the inner support tube 3 is placed, the inner support tube 3 and the fixing fixtures 6 can provide or decrease additional tension of the inner support tube 3 in the molded accommodation volume 4, and the shape of the inner support tube 3 can be thus maintained in the molded accommodation volume 4.

The front and rear surfaces of the bag 1 below the horizontal segment of the inner support tube 3 and the corresponding horizontal support segment 19 are laminated and sealed to support the inner support tube 3 thereon. This design can avoid the material within the tissue scaffold from overflowing out of the molded accommodation volume 4 to the space in the lower part of the bag 1.

In addition, the design of the horizontal segment of the inner support tube 3 and the corresponding horizontal support segment 19 of the bag 1 can adjust (the tightness of) the U-shaped support tube in the molded accommodation volume 4 by the fixing fixtures 6 without moving the fixing part of the inner support tube 3, in the elastic clamps 5. At the same time, the single-unbent-segment inner support tube can be easily disposed and fixed. In addition, the magnetic elements 14 are all disposed on the fixing rods 17, and the operation rods 18 are respectively disposed on the fixing rods 17. The magnetic elements 14 on the moving side are moved to attract or repel the magnetic elements 14 on the fixing side by operating the operation rods 18. Then, the anterior and posterior wall of the molded container around the magnetic elements 14 below the operation window 12 above the operation rod 18 may be constantly spaced or approximated.

Figure 5:
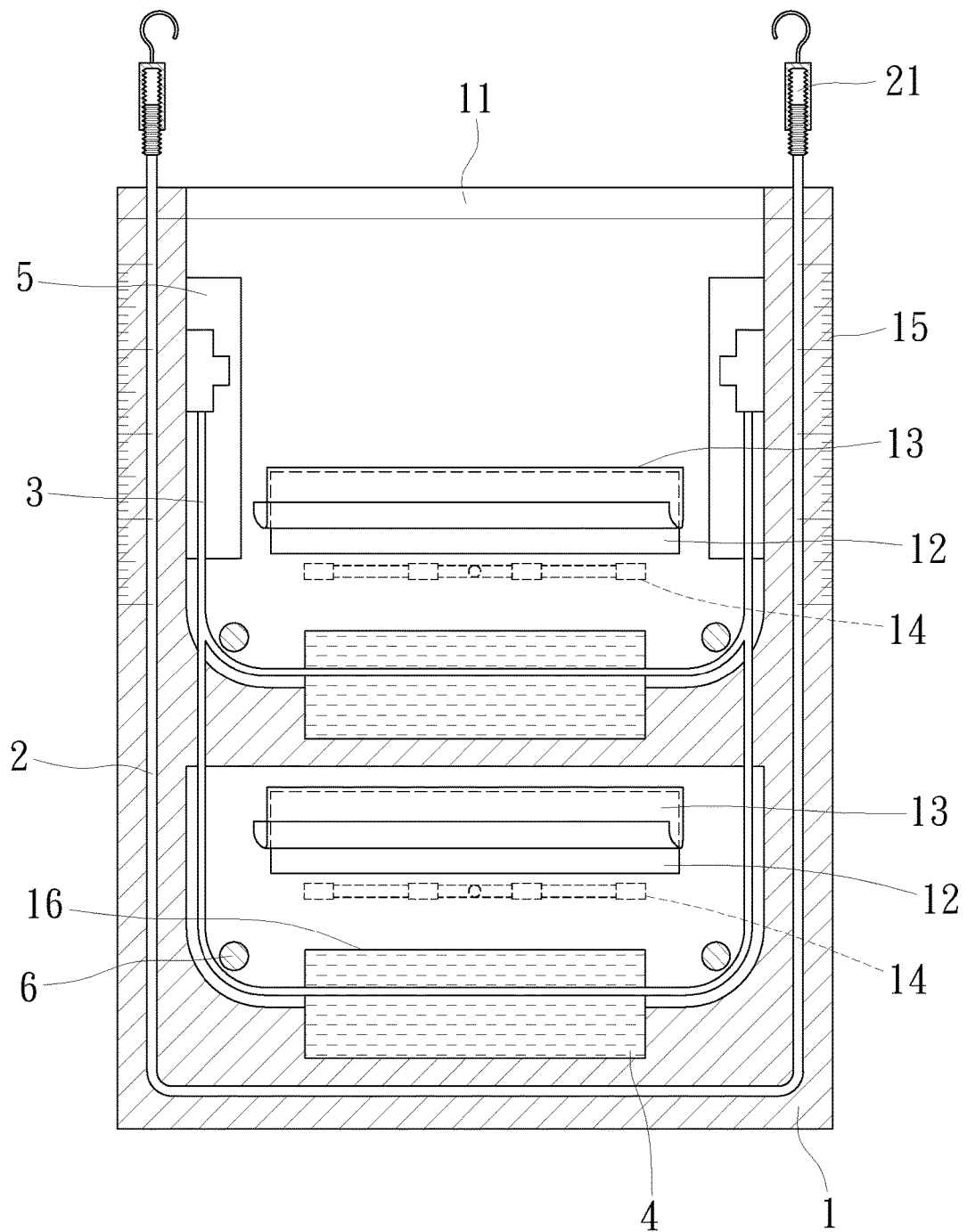
FIG. 5 is a cross-sectional diagram of a third embodiment of this invention.

Please refer to FIG. 5, which is a cross-sectional diagram of a molded container for a tissue scaffold according to a third embodiment of this invention. The molded container for a tissue scaffold may have a multi-layered design to perform multiple tissue engineering procedures at one time. The molded container comprises a bag 1 made by a soft material, a shape memory frame 2, and an inner support tube 3.

A sealing part 11 is disposed on the opening of the bag 1, and two operation windows 12 are below the sealing part 11. At least a magnetic element 14 is disposed on each of the front and rear surfaces of the bag 1 and below the operation window 12. The sealing part 11 is closed when no external forces are applied thereon. A cover 13 is disposed on the operation window 12, and the cover 13 can be peeled off or opened when the operation window 12 is used. A liquid level indicating line 16 is disposed on the external side of the bag 1.

The shape memory frame 2 is embedded in the periphery of the bag 1. The frame 2 is a metal frame made by a memory metal to maintain the shape of the frame 2. Two adjustable hook 21 are disposed on two top sides of the frame 2 and protruded out of the bag 1. The adjustable hooks 21 each having a threaded structure to adjust the bottom level of the shape memory frame 2.

The two inner support tubes 3 are respectively accommodated on the bottom and middle parts of the bag 1. Each inner support tubes 3 is selectively penetrated a molded accommodation volume 4 for forming a tissue scaffold. The molded accommodation volume 4 is a cylindrical accommodation volume or other 3D steric structures, and the length of the inner support tube 3 is longer than the length of the molded accommodation volume 4.

Here, the inner support tubes 3 are all U-shaped inner support tubes. Two elastic clamps 5 are respectively disposed on two top sides of the bag 1 to fix the two ends of the inner support tube 3. Two rulers 15 are disposed on two sides of the bag 1 to measure the relative extending length of the two terminals of the inner support tube 3. Fixed-point indication marks (not shown in FIG. 5) are disposed on the turnings of the inner support tube 3 for placing fixing fixtures 6. When the inner support tube 3 is placed, the inner support tube 3 and the fixing fixtures 6 can provide or decrease additional tension of the inner support tube 3 in the molded accommodation volume 4, and the shape of the inner support tube 3 can be thus maintained in the molded accommodation volume 4.

The front and rear surfaces of the bag 1 below the horizontal segment of the inner support tube 3 are laminated and sealed to support the inner support tube 3 thereon. This design can avoid the material within the tissue scaffold from overflowing out of the molded accommodation volume 4 to the space in the lower part of the bag 1. The inner support tube 3 in the molded accommodation volume 4 may have an irregular shape, such as cylindrical and triangular three-dimensional modeling, etc. The molded accommodation volume 4 may also have an irregular steric structure to fit the shape of the inner support tube 3.

From the embodiments above, it can be known that this invention has the following advantages, comparing with the conventional technology.

1. Adjustability: For conveniently adjusting the errors in the actual production, the vertical and horizontal position of the inner support tube and the relative position of the two ends of the inner support tube all can be rapidly adjusted. The stability after the adjustments is also considered.

2. Sterile environment: The soft bag can adjust the inner support tube to the desired position via indirectly contact by markings of rulers and positions of clamps to decrease the exposure thereof to the environment and thus the dust to form a sterile environment.

3. Stability: When the molded container is actually used, the molded container can meet the needs of the biochemical polymerization. Moreover, the design uses clamps, the support segment of the inner support tube, and the shape memory frame made from a memory metal in this invention to maintain the shape of the bag. After adding the tissue materials through the operation window, the magnetic elements can be used to rapidly close the operation window to start the polymerization in pre-designed shape.

4. Portability: The molded container can be hung in various places by using the adjustable hooks. Moreover, the bag can be made form a soft material and thus is easy to be carried.

What is claimed is:

1. A molded container for a tissue scaffold, comprising: a bag; a sealing part disposed on an opening of the bag, wherein the sealing part is closed when no external forces are applied thereon; at least an operation window disposed below the sealing part; a cover disposed on the operation window, wherein the cover can be peeled off when the operation window is used; a shape memory frame embedded in the bag having at least two adjustable hooks, which are disposed on the ends of the shape memory frame and protruded out of the bag; an inner support tube disposed on bottom in the bag, wherein the inner support tube selectively penetrates a molded accommodation volume for forming a tissue scaffold, and a length of the inner support tube is longer than a length of the molded accommodation volume.

2. The molded container for claim 1, wherein a front and a rear surfaces of the bag each has at least one magnetic element correspondingly disposed below the operation window.

3. The molded container for claim 1, wherein each of two top sides of the bag has an elastic clamp for fixing two terminals of the inner support tube, each of two sides of the bag has a ruler for measuring a relative extending length of the two terminals of the inner support tube.

4. The molded container for claim 3, wherein a turning of the inner support tube has a fixed-point indication mark.

5. The molded container for claim 1, wherein the inner support tube is a single-unbent-segment inner support tube, and two fixing fixtures are respectively disposed on two inner or outer sides of the bag for fixing the two ends of the single-unbent-segment inner support tube.

6. The molded container for claim 1, wherein the adjustable hooks have threaded structures for adjusting the bottom level of the shape memory frame.

7. The molded container for claim 1, wherein the molded accommodation volume is a cylindrical accommodation volume or other 3D steric structures.

8. The molded container for claim 7, wherein the bag has a liquid level indication line.

9. The molded container for claim 1, wherein the molded container forms a sterile enclosure.

* * * * *